United States Patent
Mundo et al.

(10) Patent No.: US 7,122,308 B2
(45) Date of Patent: Oct. 17, 2006

(54) DETECTION OF ANTIDEPRESSANT INDUCED MANIA

(75) Inventors: Emanuela Mundo, Toronto (CA); James L. Kennedy, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 506 days.

(21) Appl. No.: 10/075,249

(22) Filed: Feb. 15, 2002

(65) Prior Publication Data

US 2004/0076953 A1 Apr. 22, 2004

Related U.S. Application Data

(60) Provisional application No. 60/268,918, filed on Feb. 16, 2001, provisional application No. 60/287,128, filed on Apr. 30, 2001.

(51) Int. Cl.
*C12Q 1/68* (2006.01)
*G01N 27/26* (2006.01)
*A61K 31/137* (2006.01)

(52) U.S. Cl. .................. 435/6; 435/91.2; 204/403.01; 204/450; 204/456; 424/468; 514/649; 536/23.5

(58) Field of Classification Search ..................... None
See application file for complete search history.

(56) References Cited

U.S. PATENT DOCUMENTS

2004/0126786 A1* 7/2004 Williams

OTHER PUBLICATIONS

Bellivier et. al. Neuroscience Letters, 1998, 255:143-46.*
Chun et al. Bipolar Disorders, 2004, 6:32-42.*
Goldberg et. al. Bipolar Disorders, 2003, 5:407-420.*
McGuffin and Katz. British Journal of Psychiatry, 1989, 155:294-304.*
Mundo et. al. Biological Psychiatry [abstract], 2000, 47(suppl):135S).*
Mundo et al., Letter to the Edition of Hospital and Community Psychiatry, 44(7)689, 1993.*
Lesch K.P., et al., "Association of Anxiety-Related Traits with a Polymorphism in the Serotonin Transporter Gene Regulatory Region", Science, Nov. 20, 1996, pp. 1527-1531, vol. 274.
Howland R.H., "Induction of Mania With Serotonin Reuptake Inhibitors", Journal of Clinical Psychopharmacology, 1996, pp. 425-427, vol. 16, No. 16.
Solomon R.L., et al., "Antidepressant treatment and the occurrence of mania in bipolar patients admitted for depression", Journal of Affective Disorders, 1990, pp. 253-257, vol. 18.
Hoehe M.R., et al., "Serotonin Transporter (5-HTT) Gene Polymorphisms Are Not Associated With Susceptibility to Mood Disorders", American Journal of Medical Genetics (Neuropsychiatric Genetics), 1998, pp. 1-3, vol. 81.
Mundo E., et al., "Lack of Linkage Disequilibrium Between Serotonin Transporter Protein Gene (SLC6A4) and Bipolar Disorder", American Journal of Medical Genetics (Neuropsychiatric Genetics), 2000, pp. 379-383, vol. 96.
Mundo E., et al., "The Role of Serotonin Transporter Protein Gene in Antidepressant-Induced Mania in Bipolar Disorder (Preliminary Findings)", Arch Gen Psychiatry, Jun. 2001, pp. 539-544, vol. 58.

* cited by examiner

*Primary Examiner*—Janet L. Andres
*Assistant Examiner*—Michael Brannock
(74) *Attorney, Agent, or Firm*—Micheline Gravelle; Bereskin & Parr

(57) ABSTRACT

Methods and kits for assessing the susceptibility of a patient to antidepressant-induced mania are described. The method involves testing a sample from a patient for the presence of the s variant of the 5HTTLPR polymorphism in the 5HTT gene. The presence of this s variant indicates that the patient is more susceptible to antidepressant-induced mania.

4 Claims, 2 Drawing Sheets

FIGURE 1 ctaatgtccctactgcagccctcccagcatcccccctgcaacctcccagcaactccctgta ccnctcctaggatcgctcctgcatcccccattatccccccttcacccctcgcggcatcccc cctgcaccccagcatcccccctgcagcccttccagcatcccctgcacctctcccaggat attccctgcaacacncattattcccctgcaccctcgcagtattcccctgcaccccag catccccccatgcaccccggcatcccccctgcaccctccagcattctccttgcaccta ccagtattcccccgcatcccggcctccaagcctccgcccgacctctgtcaccgccctg Legend:

ss= subject homozygous for the short allele; sl= subject heterozygous; ll= subject homozygous for the long allele.

DETECTION OF ANTIDEPRESSANT INDUCED MANIA

This application claims the benefit under 35 USC §119(e) from U.S. provisional patent application Ser. No. 60/268,918, filed Feb. 16, 2001 and U.S. provisional patent application Ser. No. 60/287,128, filed Apr. 30, 2001.

FIELD OF THE INVENTION

The present invention relates to methods and kits for determining the susceptibility of a patient to antidepressant-induced mania.

BACKGROUND OF THE INVENTION

The induction of mania in patients treated with antidepressants is a complex and not rare phenomenon, which has been described to occur with different frequencies in Bipolar Disorder (BP), Unipolar Disorder (UP), and Obsessive-Compulsive Disorder (OCD) (1–8). In Mood Disorder (MD) patients, the frequency of induction of mania during antidepressant treatment has been estimated to be 9.5–33%, varying in the different studies including different diagnoses (i.e. UP and BP) and different antidepressant treatments (9–11). More recently, it has become clearer that the phenomenon of antidepressant-induced mania is strictly related to a diagnosis of BP. In BP patients the switch rate during antidepressant treatment is definitively higher than in UP patients (12) and represents a critical issue for the long-term management of the disorder. Whether the type of antidepressant treatment can affect the risk of developing manic switches remains controversial. According to the report of Solomon et al (2), an antidepressant-induced manic episode occurs in approximately 20% of the inpatient admissions with a diagnosis of BP, independently from the treatment status (tricyclic antidepressants -TCAs-, monoamine oxidase inhibitors -MAOIs- or electroconvulsive therapy -ECT-). On the other hand, some studies have shown that the rate of induction of mania is higher in BP patients treated with TCAs and MAOIs than in BP patients treated with selective serotonin reuptake inhibitors (SSRIs) (8, 13).

As the impact on the natural course of BP and on the clinical management of the disease created by the occurrence of antidepressant-induced manic switches is quite high (1, 14), the detection of poss predictors of this phenomenon has become one of the primary goals of clinical studies. A higher number of previous manic or hypomanic episodes appeared to be the only clinical variable affecting the risk for developing induced mania during antidepressant treatment (8, 12). According to the report of Stoll et al. (15) antidepressant-induced manic/hypomanic episodes appear to be also clinically different from the spontaneous ones, usually having a shorter duration and less severe psychotic symptoms (15).

Most of the antidepressants commonly used to treat the depressive episodes that occur in the course of BP, act on the serotonin transporter (5HTT) (16). The 5HTT is located on the terminals of serotonergic neurons and its function is to reuptake serotonin from the synaptic cleft into the cell (16). Family, twin, and molecular genetic studies, have shown that BP has a strong genetic component (17–20), and thus, the 5HTT protein gene has been considered an good candidate for the investigation of the genetic component of both BP and the response to antidepressant medication.

The 5HTT gene is located on Chromosome 17, spans 31 kilobases (KB) and consists of 14 exons. This gene has two polymorphisms known. One is in the promoter region (5HT-TLPR) consisting of 44 bp insertion/deletion (21). Studies employing lymphoblastoid cell lines containing different genotypes with respect to the 5-HTTLPR (21) showed that cells homozygous for the 1 allele produced steady-state concentrations of 5-HTT mRNA that were 1.4 to 1.7 times those in cells containing 1 or 2 copies of the s. At the protein level, membrane preparations from l/l lymphoblasts bound 30% to 40% more of a labeled marker than did membranes from l/s or s/s cells. Moreover, uptake of labeled serotonin in cells homozygous for the l allele of the promoter polymorphism was 1.9 to 2.2 times that in cells carrying 1 or 2 endogenous copies of the s variant. These data also suggested that the polymorphism has more of a dominant-recessive than a codominant-additive effect. in rare circumstances, particularly in Asian and African-American populations, additional variants such as the vl (very long) allele and the xl (extra long) allele may occur (22).

Investigation for the possible involvement of the 5HTTLPR in the pathogenesis of BP, applying different methods, has lead to conflicting results. Two linkage studies to date using multiplex families have provided negative results (23–24). Among the several case-control association studies performed, only two studies detected a positive association between the s variant of the gene and BP (25–26). Two studies applying strategies for the detection of association in presence of linkage disequilibrium, which are particularly useful for assessing gene susceptibility in psychiatric disorders where genes may be of small effect (27), gave negative results (28–29).

The other polymorphism known for the 5HTT gene is a variable number of tandem repeats (VNTR) polymorphism in the second intron, with three alleles (Stin2.9, Stin2.10 and Stin2.12) (30). The Stin2.12 allele was found to be associated with BP in two studies (25, 31), while more recent studies appear to exclude any associations between this polymorphism and BP (32–35).

At least three studies to date have considered the two known polymorphisms of the 5HTT gene in a haplotype analysis, with negative results (26, 35, 36).

With respect to the role of the 5HTTLPR in the antidepressant response, patients with Major Depression and homozygous or heterozygous for the l variant appear to show a better response to fluvoxamine (37) and paroxetine (38) and patients with Bipolar Depression who are homozygous for the l variant of the 5HTTLPR have been found to have a better clinical response to total sleep deprivation (39).

On the other hand, the meaning of these findings, as well as the relationships with the functional variations associated with the gene are controversial (40).

SUMMARY OF THE INVENTION

The present inventors have determined that there is correlation between the presence of a polymorphism in the serotonin transporter 5HTT gene and the occurrence of antidepressant-induced mania. In particular, the inventors have shown that a DNA sequence variant in the promoter region of 5HTT (5HTTLPR) consisting of a 44 bp deletion in the gene (which is called the s variant) appears to be involved in the pathogenesis of manic/hypomanic switches in a bipolar patients treated with pro-serotonergic antidepressant agents.

Accordingly, the present invention provides a method of determining the susceptibility of a patient to antidepressant-induced mania comprising:
(a) obtaining a sample from the patient; and
(b) testing the sample for the presence of the s variant of the 5HTTLPR polymorphism in the 5HTT gene, wherein the presence of the s variant indicates that the patient is more susceptible to antidepressant-induced mania.

The patient is preferably a patient with Bipolar Disorder who has been treated with a proserotonergic agent.

The present invention also provides a kit for determining the susceptibility of a patient to antidepressant-induced mania comprising reagents necessary for determining the presence of the s variant of the 5HTTLPR polymorphism and directions for its use.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows the nucleic acid sequence of the s variant of the 5HTTLPR gene (SEQ ID NO:1).

DETAILED DESCRIPTION OF THE INVENTION

Figure 2:
FIG. 2 is an electrophoresis gel showing the size of the s variant of the 5HTTLPR gene.

The occurrence of mania during antidepressant treatment is a critical issue in the clinical management of Bipolar Disorder (BP). The serotonin transporter (5HTT) is the selective site of action of most of the pro-serotonergic compounds used to treat bipolar depression. The 5has two known polymorphisms. One is functional and consists of 44 bp insertion/deletion in the promoter region (5HTTLPR), and the other one consists of a variable number of tandem repeats (VNTR) within the second intron. The present inventors have investigated the role of 5HTT gene variants in the pathogenesis of antidepressant-induced mania in BP and the results of this investigation have been peer-reviewed and published in the Archives of General Psychiatry (50).

Twenty-seven patients with a DSM-IV diagnosis of BPI or BPII, with at least one manic or hypomanic episode induced by treatment with pro-serotonergic antidepressants (IM+) were compared to 29 unrelated matched BPI or BPII patients, who never developed manic or hypomanic episodes during the exposure to pro-serotonergic antidepressants (IM−). The two polymorphisms of the 5HTT gene were genotyped with standard procedures, and allelic and genotypic association analyses were done. While no association was found with the VNTR polymorphism, with respect to the 5HTTLPR polymorphism, among IM+ patients there was an excess of the short allele (chi-square=12.770, df=1, p=.0004), a higher rate of homozygosity for the short variant and a lower rate of homozygosity for the long variant (chi-square=12.432, df=2, p=.002). As a result, the 5HTTLPR polymorphism is an important predictor of abnormal response to medication in BP patients.

In particular, the inventors have shown that the s variant of the poly morphism in the promoter region 5HTTLPR is involved in the pathogenesis of manic/hypo-manic switches in a bipolar patients treated with pro-serotonergic agents.

Accordingly, the present invention provides a method of determining the susceptibility of a patient to antidepressant-induced mania comprising:
(a) obtaining a sample from the patient; and
(b) testing the sample for the presence of the s variant of the 5HTTLPR polymorphism in the 5HTT gene, wherein the presence of the s variant indicates that the patient is more susceptible to antidepressant-induced mania.

The term "s variant of the 5HTTLPR gene" means a 44 bp deletion in the promoter region of the 5HTT gene. The nucleic acid sequence of the s variant is shown in FIG. 1. (The sequence is from Cook et al., 1997.)

The patient is any patient being treated with antidepressants, preferably a patient with Bipolar Disorder who is being treated with an antidepressant that acts directly or indirectly on the 5HTT sites. The examples of such antidepressants include, but are not limited to, clornipramine, fluvoxamine, fluoxetine, paroxetine, sertraline, citalopram, imipramine, nefazodone, venlafaxine or moclobemide.

The sample obtained from the patient can be any biological sample containing nucleic acids including, but not limited to, blood, urine, skin, hair, sperm, buccal mucosa as well as tissue samples and fractions of any of the foregoing.

The sample may be tested for the presence of a polymorphism in the 5HTT gene using a variety of techniques known in the art. Generally, nucleic acids are obtained from the sample and amplified using the Polymerase Chain Reaction (PCR) using primers to the appropriate region of the 5HTT gene. For example when assaying for polymorphisms in the promoter region primers to the promoter region are used. The PCR products can be subjected to any method that would allow one to identify the presence of a polymorphism. In one embodiment, the PCR products may be subjected to an electrophoretic assay (such as gel electrophoresis or capillary electrophoresis) to determine the relative size of the PCR product. For example, the s variant of 5HTTLPR has a size of 406 bp which can be determined by comparing its migration on an electrophoresis gel with a 50 bp ladder (See Example 1, FIG. 2). In another embodiment, the PCR products may be probed with a nucleic acid sequence specific for a region in the polymorphism. In a further embodiment, the PCR products may be sequenced using techniques known in the art including commercially available sequencing kits to determine if the polymorphism is present in the sample. Other sequencing technologies such as Denaturing High Pressure Liquid Chromatography or mass spectroscopy may also be employed. In yet another embodiment, detection of polymorphism can be performed by using restriction enzymes or Single Stranded Conformation Polymorphism (SSCP) techniques. In addition, methods for high throughput detection of nucleotide polymorphisms may be used such as DNA chip technology. Combinations of any of the above methods may be used.

The invention also includes kits for use in the above methods for detecting the presence of the s variant of the 5HTTLPR polymorphism. Accordingly, the present invention provides a kit for determining the susceptibility of a patient to antidepressant-induced mania comprising reagents necessary for determining the presence of the s variant of the 5HTTLPR polymorphism and directions for its use. The reagents useful in the kit can be determined by one of skill in the art and can include primers to the appropriate regions of the 5HTT gene in order to amplify nucleic acids from a test sample using PCR. The kit may further include nucleic acid probes useful in determining the presence of the s variant. The kit may also include electrophoretic markers such as a 50 bp ladder. Other components of the kit can include nucleotides, enzymes and buffers useful in a method of the invention. As an example, a kit of the invention may include primers for amplifying the region surrounding the s variant, DNA polymerase, each of dATIP, dTTP, dCTP and dGTP, 7-deaza-dGTP, 10 mM Tris-HCl, 50 mM KCl, 1.5 mM $MgCl_2$ and 5% DMSO. Furthermore, the kit may include DNA sequencing reagents and fluorescent dyes or other labeling chemicals. The kit will also include detailed instructions for carrying out the method for detecting the presence of the s variant of the 5HTT gene.

The following non-limiting examples are illustrative of the present invention:

EXAMPLE

Example 1

Subjects and Methods

Subjects

The subjects investigated for the purpose of this study have been selected from a larger sample of 300 Bipolar I or Bipolar II patients recruited from hospital clinics and newspaper advertisements in Toronto and across Central Canada, within the research protocols of our group. To all these patients the diagnostic structured interview for DSM-IV Axis I diagnoses (SCID-I) (41) and the Family Interview for Genetic Studies (FIGS) (42) had been administered by trained interviewers. From all patients and their parents, written informed consent to participate in the studies was obtained.

The SCID-1, the FIGS. , the clinical and the life charts available, and also all the information about the past and the current pharmacological treatment recorded during the interviews were blindly and independently reviewed by two trained psychiatrists (E.M., J. L. K.). To avoid investigators biases, only information and life charts that existed before the design of the present investigation have been used.

Based on this review, from the original sample two groups of unrelated patients were selected. The first group was comprised of 27 subjects with a positive history for antidepressant-induced mania (IM+), and it was composed by patients with the following characteristics: 1) a confirmed DSM-IV diagnosis of Bipolar I or Bipolar II Disorder; 2) at least one depressive episode treated with pro-serotonergic antidepressants; and 3) at least one manic or hypomanic episode induced by the treatment with these compounds (i.e. one episode fulfilling DSM-IV criteria for either mania or hypomania, developed during antidepressant treatment). The second group (IM−) consisted of 29 patients with the following characteristics: 1) a confirmed diagnosis of Bipolar I or Bipolar II Disorder; 2) at least one depressive episode treated with pro-serotonergic antidepressants; and 3) no antidepressant-induced manic or hypomanic episodes.

Patients within the IM− group were matched by sex, age (±5 years), and ethnicity with the patients of the IM+ group.

Subjects with 1) uncertain DSM-IV diagnosis of BP (including patients with only one manic or hypomanic episode induced by antidepressant treatment and no spontaneous ones, for whom there is up to the time of assessment no consensus regarding the diagnosis of BP), and/or 2) unavailable, inadequate, or unreliable information on the past and the current psychopharmacological treatments, and/or 3) no history of exposure to pro-serotonergic antidepressants, were excluded.

For both of the two groups of patients (IM+ and IM−) the following demographic and clinical variables were collected from the SCID and the FIGS: age at the time of the interview, the age at onset of BP, the diagnostic subtype of BP, the comorbid Axis I diagnoses, the number of spontaneous manic or hypomanic episodes, the number of depressive episodes, the presence/absence of psychotic symptoms during the mood episodes, the presence/absence of rapid cycling, and the family history for Mood Disorders.

Information about current or past treatment with mood stabilizers was also recorded from the clinical charts, where available.

Genotyping

Genomic DNA was extracted from blood using a non-enzymatic procedure (43).

All the genotyping procedures have been performed blindly with respect to the aim, the design of this study, and the clinical diagnoses of the subjects investigated.

a. 5HHTLPR

Polymerase chain reaction (PCR) was used to amplify a segment of genomic DNA containing the insertion/deletion polymorphism in the promoter region of the serotonin transporter using primers with the sequences reported in Cook et al. (44). The PCR reaction was performed in a 25 uL volume containing: 200 ng genomic DNA, 10 mM Tris-HCl, 50 mM KCl, 1.5 mM $MgCl_2$, 5% DMSO, 200 µM each of dATP, dTTP, and dCTP, 100 µM of dGTP, 100 µM of 7-deaza-dGTP, 1 µM of each primer, and 1 unit of Amp/iTaq DNA polymerase. The genomic DNA was denaturated at 95° C. for 3 min, then the remaining reaction components were added. The reaction consisted of 40 cycles of: 95° C. for 30 sec, 61° C. for 30 sec, 71° C. for 60 sec, followed by extension at 72° C. for 10 min. PCR products were subjected to electrophoresis on a 2.5% agarose gel and visualized under ultraviolet light in the presence of ethidium bromide. DNA bands were assigned allele numbers based on their size [allele 1 (l)=450 bp; allele 2 (s)=406 bp], which was determined by comparing their migration in the gel with a 50 bp ladder as shown in FIG. 2.

b. VNTR

This polymorphism was also amplified using a modified protocol from Cook et al (44). The 25 µl reaction consisted of 200 ng template, 0.8 µl of each primer, 1X PCR buffer, 1 mM $MgCl_2$, 0.2 mM each of dATP, dCTP, and dTTP, 0.15 mM dGTP and 0.05 mM 7-deaza-dGTP, 8% DMSO, and 1U Taq polymerase. Cycling conditions consisted of initial denaturation for 3 min at 95° C. followed by 40 cycles of 45 s denaturation at 95° C., 30 s annealing at 56° C., and a 45 s extension at 72° C. ending with a final 7 min extension at 72° C. After separation on a 2.5% agarose gel for 2 hours at 100V the three alleles produced bands at 345 bp (9 repeats), 360 bp (10 repeats), and 390 bp (12 repeats).

Statistical Analysis

All the demographic and clinical variables available were tabulated and compared between the two samples of patients studied. The Student's t-test (two-tailed) for independent samples was used for the continuous variables, while the chi-square was used for the dichotomous ones.

The genotype data for both polymorphisms were analyzed with chi-square tests. Both allele and genotype frequencies were compared between the two groups (IM+ and IM−).

Results

The main demographic and clinical variables for the two samples of patients are summarized in Table 1. No significant differences were found between the two groups with respect to the variables considered.

Data regarding past or current treatment with mood stabilizers (lithium, carbamazepine or valproate) were available for 50 patients, 23 in the IM+ group and 27 in the IM− group. In the IM+ group for 10 patients there was information available regarding the time of the induction of mania during the exposure to antidepressants: 5 were on mood stabilizers, five were not. In the IM− group 20 patients were on mood stabilizers at the time of the exposure to the antidepressant treatment, but the majority of them (N=13) had spontaneous manic episodes while on mood stabilizers.

In the IM+ group the antidepressant treatments ongoing during the development of manic/hypomanic episodes were: fluoxetine (N=8), fluvoxamine (N=6), fluoxetine+fluvoxamine (N=3), paroxetine (N=2), nefazodone (N=2), moclobemide (N=2), imipramine (N=2), venlafaxine (N=1) and sertraline (N=1).

In both IM+ and IM− groups 96.3% of the subjects were Caucasian, and 3.7% were East Asian.

For the 5HTTLPR polymorphism the genotype frequencies in the whole sample were: ll=30.4% (N=17), ls=48.2% (N=27), and ss=21.4% (N=12). Data for the VNTR polymorphism were available for 54 out of the 56 patients who comprised the total sample studied, resulting in the following genotype frequencies: Stin2.9-Stin2–10=1.9% (N=1), Stin2.9Stin2.12=1.9% (N=1), Stin2.10-Stin2.10=9.6% (N=5), Stin2.10-Stin2.12=44.4% (N=24), Stin2.12-Stin2.12=42.6% (N=23). The whole sample and the two sub-samples (IM+ and IM−) were in Hardy-Weinberg equi polymorphisms studied.

Table 2 summarizes the genotypes and allele frequencies for the two polymorphisms studied in the two samples of patients. Results of the association analysis performed with both the alleles and the genotypes of the VNTR polymorphism did not show any significant difference between the two groups of patients. Regarding the 5HTTLPR polymorphism, the allelic association analysis showed that among IM+ patients there was an excess of the s allele (Pearson chi-square=12.770, df=1, p=.0004). The association analysis performed with the genotypes was also significant, showing a higher rate of homozygosity for the s variant and a lower rate of homozygosity for the l variant among IM+ patients (Pearson chi-square=12.432, df=2, p=0.002). The approximate Relative Risk associated with the presence of the s variant has been estimated as 4.1 (table 2).

Discussion

According to the results presented in this example, the presence of the s variant of the 5HTTLPR confers a higher risk to develop antidepressant-induced mania in BP patients treated with pro-serotonergic compounds.

According to Lesch et al. (21) the presence of this variant implies a lower expression of the gene: the uptake of 5HT is less in cells carrying 1 or 2 copies of the s allele than in cells homozygous for the l allele, and the ll cells produce steady-state concentrations of 5HTT mRNA that are up to 1.7 times the concentrations in both ls and ss cells.

The relationship between this functional variation and the clinical effects of antidepressants is still unclear.

With respect to the finding regarding the effect of the 5HTTLPR polymorphism on the pathogenesis of antidepressant-induced mania, while not wishing to be limited by theory, it is hypothesized that our BP patients homozygous for the s variant, having fewer 5HTT sites, could be more sensitive to either the blockade of 5HT reuptake or to the increase of 5HT availability. Both these effects had been induced by the antidepressant medication in the IM+ sample during the treatment with SSRIs (fluvoxamine, fluoxetine, paroxetine, or sertraline), or other pro-serotononergic antidepressants including imipramine, nefazodone, venlafaxine or moclobemide. All these compounds, which are referred to as "pro-serotonergic antidepressants", directly or indirectly act on 5HT neurotransmission (16, 45, 46).

If this hypothesis is true, patients with the ss genotype should also be more likely either to respond to pro-serotonergic antidepressants or to show a shorter latency for the response itself.

On the other hand, the s variant of the 5HTTLPR has been found to be associated with poor response to antidepressant treatment either with SSRIs (37, 38) or with total sleep deprivation (39). It has been commented (40) that subjects homozygous for this variant have a lower number of 5HTT sites and, thus, have higher serotonin (5HT) levels in the synaptic cleft. This situation induces a higher inhibition of 5HT release by 5HT pre-synaptic autoreceptors, with the final result of a reduction of the overall serotonergic neurotransmission predisposing to a poorer response to SSRIs. This hypothesis appears to be confirmed by the fact that patients homozygous for the ls variant and treated with adjuvant pindolol (a selective blocker of 5HT/IA autoreceptors) respond to SSRIs similarly to patients homozygous for the l variant (37). On the other hand, this explanatory hypothesis could be accepted only if it is assumed that the pre-synaptic autoreceptors are not "down-regulated" by the increase of 5HT in the synaptic cleft. Moreover, the situation appears to be even more controversial considering a recent report by him et al (47), which associates a good response to SSRIs with the ss genotype. It is quite likely that the lack of homogeneity across these different studies, with respect to the diagnosis (BP or UP), to the compounds administered, or to the definition of the antidepressant response, have been reflected in discordant results. Further studies are needed to clarify these issues. Whether, for example, in BP the antidepressant-induced manic switches should be considered phenomena quantitatively or qualitatively different from the expected antidepressant response is still unclear.

On the other hand, according to the information extracted from the sample, there were no significant differences between IM+ and IM− with respect to the concomitant treatment with mood stabilizers, the variable that would have the most impact on the risk of developing manic switches during the antidepressant treatment. Moreover, even though in the IM− group the percentage of patients on mood stabilizers at the time of the exposure to the antidepressant treatment was higher than that in the IM+ group, most of the IM− developed spontaneous manic or hypomanic episodes despite being on lithium, carbamazepine, or valproate. Thus, the treatment with mood stabilizers is not likely to have been a protective factor with respect to manic switches during antidepressant treatment, at least in this sample. The doses and the treatment duration for the pro-serotonergic antidepressants administered were also not controlled in our samples. On the other hand, there are no studies, to the inventors' knowledge, showing that antidepressant-induced manic/hypomanic episodes are related to these variables.

Ideal study designs on the possible predictors of antidepressant-induced manic switches, would imply the random and "blind" exposure drug-naive BP patients to antidepressants and mood stabilizers, but these studies have obvious ethical and practical limitations. This is the main reason why the studies performed to date to investigate the possible predictors and the clinical characteristics of antidepressant-induced mania have been done according to naturalistic designs (8, 12, 15).

The above Example suggests a role of the 5HTTLPR polymorphism in the pathogenesis of antidepressant-induced mania in BP. Therefore, the 5HTTLPR polymorphism may become an important predictor of the antidepressant-induced manic switches, which are among the most clinically relevant side effects of the antidepressant treatment in BP patients.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Summary of the main demographic and clinical variables in the two groups of patients, with (IM+) and without (IM−) antidepressant-induced manic/hypomanic episodes.

|  | IM+ (N = 27) | IM− (N = 29) |
|---|---|---|
| Gender | 9 M, 18 F | 9 M, 20 F |
| Age | 36.3 (8.5) | 36.3 (7.7) |
| Age at Onset | 19.8 (5.5) | 19.5 (6.2) |
| Principal Axis I Diagnosis: |  |  |
| Bipolar I | 15 (55.5%) | 19 (65.5%) |
| Bipolar II | 12 (44.5%) | 10 (34.5%) |

TABLE 1-continued

Summary of the main demographic and clinical variables in the two groups of patients, with (IM+) and without (IM−) antidepressant-induced manic/hypomanic episodes.

|  | IM+ (N = 27) | IM− (N = 29) |
|---|---|---|
| Axis I Comorbidity[1] |  |  |
| None | 12 (44.4%) | 16 (55.1%) |
| Obsessive-Compulsive Disorder | 6 (22.2%) | 3 (10.3%) |
| Panic Disorder | 5 (18.5%) | 5 (17.2%) |
| Social Phobia | 3 (11.1%) | 1 (3.4%) |
| Simple Phobia | — (0%) | 1 (3.4%) |
| Alcohol Abuse/Dependence | 2 (7.4%) | 1 (3.4%) |
| Substance Abuse/Dependence | 1 (3.7%) | 1 (3.4%) |
| Post-Traumatic Stress Disorder | 1 (3.7%) | 2 (6.9%) |
| Generalized Anxiety Disorder | — (0%) | 1 (3.4%) |
| Family History for Mood Disorders[2] |  |  |
| Negative | 5 | 9 |
| Bipolar Disorder | 12 | 11 |
| Major Depressive Disorder | 9 | 6 |
| N. Depressive Episodes | 5.9 (4.6) | 4.5 (2.35) |
| N. Manic/Hypomanic Episodes | 3.8 (1.8) | 3.7 (2.1) |
| Psychotic Features (N) | 19 (70.4%) | 15 (51.7%) |
| Rapid Cycling (N) | 3 (11.1%) | 2 (6.9%) |

Notes:
SD are shown in parentheses for continuous variables.
[1]The total exceeds 100% because of multiple diagnoses.
[2]Data were not available for 4 patients.

TABLE 2

Genotype and allele frequencies for the two polymorphisms of the 5HTT gene in the two groups of patients with (IM+) and without (IM−) antidepressant-induced manic/hypomanic episodes.

|  | IM+ (N = 27) | IM− (N = 29) |
|---|---|---|
| 5HTTLPR |  |  |
| Alleles: |  |  |
| l | 20 (37.0%) | 41 (70.7%)* |
| s | 34 (63.0%) | 17 (29.3%)* |
| Genotypes: |  |  |
| ll | 3 (11.1%) | 14 (48.3%)** |
| ls | 14 (51.9%) | 13 (44.8%)** |
| ss | 10 (37.0%) | 2 (6.9%)** |
| VNTR[1] |  |  |
| Alleles: |  |  |
| Stin2.9 | 2 (4%) | 0 (0%) |
| Stin2.10 | 12 (24%) | 23 (39.6%) |
| Stin2.12 | 36 (72%) | 35 (60.3%) |
| Genotypes: |  |  |
| Stin2.9-Stin2.10 | 1 (4%) | 0 (0%) |
| Stin2.9-Stin2.12 | 1 (4%) | 0 (0%) |
| Stin2.10-Stin2.10 | 1 (4%) | 4 (13.8%) |
| Stin2.10-Stin2.12 | 9 (36%) | 15 (51.7%) |
| Stin2.12-Stin2.12 | 13 (52%) | 10 (34.5%) |

Notes:
[1]VNTR genotyping was missing in 2 patients of the IM+ group, thus the percentages in this group have been computed on a total of 25 patients.
*Pearson chi-square = 12.770, df = 1, p = .0004 (2-sided); Likelihood Ratio = 13.013, df = 1, p = .000 (two-sided); Fisher's Exact Test: p = .001 (2-sided). Odds ratio = 4.1.
**Pearson chi-square = 12.432, df = 2, p = .002 (2-sided); Likelihood Ratio = 13.511, df = 2, p = .001 (2-sided).

FULL CITATIONS FOR REFERENCES REFERRED TO IN THE SPECIFICATIONS

1. Wehr T A, Goodwin F K. Can antidepressants cause mania and worsen the course of affective illness? Am J Psychiatry. 1987; 144: 1403–1411.
2. Solomon R, Rich C L, Darko D F. Antidepressant treatment and occurrence of mania in bipolar patients admitted for depression. J Affective Dis. 1990; 18: 253–257.
3. Vieta E, Bernardo M. Antidepressant-induced mania in obsessive-compulsive disorder. Am J Psychiatry. 1992; 149(9): 1282–1283.
4. Mundo E, Ronchi P, Bellodi L. Obsessive-compulsive patients at risk for antidepressant-induced mania. Hosp Comm Psychiatry. 1993; 44:7: 689–690.
5. Diaferia G, Mundo E, Bianchi Y, Ronchi P (1994). Behavioral side effects in obsessive-compulsive patients treated with fluvoxamine: a clinical description. J Clin Psychopharmacol. 1994; 14(1): 78–79.
6. Altshuler L L, Post R M, Leverich G S, Mikalauskas K, Rosoff A, Ackerman L. Antidepressant-induced mania and cycle acceleration: a controversy revisited. Am J Psychiatry. 1995; 152(8): 1130–1138.
7. Howland R H. Induction of mania with serotonin reuptake inhibitors. J Clin Psychopharmacol. 1996; 16: 425–427.
8. Boerlin H L, Gitlin M J, Zoellner L A, Hammen C L. Bipolar Depression and antidepressant-induced mania: a naturalistic study. J Clin Psychiatry. 1998; 59: 374–379.
9. Bunney W E. Psychopharmacology of the switch process in affective process. In: Psychopharmacology: a generation of progress. Lipton M A, Damascio A, Kellam K F (eds). New York, Raven Press; 1978: pp 1249–1259.
10. Prien R F, Klett J, Coffey E M. Lithium carbonate and imipramine in prevention of affective episodes: a comparison in recurrent affective illness. Arch Gen Psychiatry. 1973; 29: 420–425.
11. Lewis J L, Winkour G. The induction of mania. Arch Gen Psychiatry. 1982; 39: 303–306.
12. Angst J. Switch from depression to mania- A record survey over decades between 1920 and 1982. Psychopathology. 1985; 18: 140–154.
13. Peet M. Induction of mania with selective serotonin reuptake inhibitors and tricyclic antidepressants. Br J Psychiatry. 1994; 164: 549–550.
14. Goodwin F K, Jamison K R. Manic Depressive Illness. New York, Oxford University Press; 1990; pp.642–647.
15. Stoll A I, Mayer P V, Kolbrener M, Goldstein E, Suplit B, Lucier J, Cohen B M, Tohen M. Antidepressant-associated mania: a controlled comparison with spontaneous mania. Am J Psychiatry. 1994; 151: 1642–1645.
16. Blier P, de Montigny C. Possible serotonergic mechanisms underlying the antidepressant and anti-obsessive-compulsive disorder responses. Biol Psychiatry. 1998; 44: 313–323.
17. McGuffin P, Katz R. The genetics of depression and manic-depressive disorder. Br J Psychiatry. 1989; 155: 294–304.
18. Gershon E S. Genetics. In Goodwin F K, Jamison K R (eds) Manic-Depressive Illness. Manic Depressive Illness. New York, Oxford University Press; 1990; pp.373–401.
19. Nurnberger Jr J I, Gershon E S. Genetics. In Paykel E S (ed) Handbook of Affective Disorders. London, Churchill Livingstone; 1992, pp.131–148.
20. Craddock N, Jones I. Genetics of Bipolar Disorder. J Med Genet. 1999; 36: 585–594.
21. Lesch K P, Bengel D, Heils A, Sabol S Z, Greenberg B D, Petri S, Benjamin J, Muller C R, Hamer D H, Murphy D L. Association of anxiety-related traits with a polymorphism in the serotonin transporter gene regulatory region. Science. 1996; 274: 1527–1530.
22. Gelernter J, Kranzler H, Cubells J F. Serotonin transporter protein (SLC6A4) allele and haplotype frequencies and linkage disequilibria in African- and European-American and Japanese populations and in alcohol dependent subjects. Hum Genet. 1997; 101: 243–246.
23. Kelsoe J R, Remick R A, Sadovnick A D, Kristbjarnarson H, Flodman P, spence M A, Morison M et al. Genetic linkage study of bipolar disorder and the serotonin transporter. Am J Med Genet.1996; 67(2): 215–217.
24. Ewald H, Flint T, Degn B, Mors 0, Kruse T A. A functional variant of the serotonin transporter gene in families with bipolar affective disorder. J Affect Disord. 1998; 48(2–3): 135–144.
25. Collier D A, Stober G, Li T, Heils A, Catalano M, Di Bella D, Arranz M J, Murray R M, Vallada H P, Bengel D, Muller C R, Roberts G W, Smeraldi E, Kirov G, Sham P, Lesch K P. A novel functional polymorphism within the promoter of the serotonin transporter gene: possible role in susceptibility to affective disorders. Mol Psychiatry.1996; 1(6): 453–460.
26. Bellivier F, Henry C, Szoke A, Schurhoff F, Nosten-Bertrand M, Feingold J, Launay J M, Leboyer M, Laplanche J L. Serotonin transporter gene polymorphisms in patients with unipolar or bipolar depression. Neuroci Lett. 1998; 255(3): 143–146.
27. Risch N, Merikangas K. The future of genetic studies on complex human diseases. Science 1996; 273:1516–1517.
28. Esterling L E, Yoshikawa T, Turner G, Badner J A, Bengel D, Gershon E S, Berrettini W H, Detera-Wadleigh S D. Serotonin transporter (5HTT) gene and bipolar affective disorder. Am J Med Genet. 1998; 81(1): 37–40.
29. Mundo E, Walker M, Tims H, Macciardi F, Kennedy J L. Lack of linkage disequilibrium between serotonin transporter protein gene (SCL6A4) and Bipolar Disorder. Am J Med Genet. 2000; 96: 379–383.
30. Ogilvie A D, Battersby S, Bubb V J, Fink G, Harmar A J, Goodwin G M, Smith CAD. Polymorphism in serotonin transporter gene associated with susceptibility to major depression. Lancet. 1995; 347: 731–733.
31. Kunugi H, Hattori M, Kato T, Tatsumi M, Sakai T, Sasaki T, Hirose T, Nanko S. Serotonin transporter gene polymorphisms: ethnic difference and possible association with bipolar affective disorder. Mol Psychiatry. 1997; 2(6): 457–462.
32. Rees M, Norton N, Jones I, McCandless F, Scourfield J, Holmans P, Moorhead S, Feldman E, Sadler S, Cole T, Redman K, Farmer A McGuffin P, Owen M J, Craddock N. Association studies of bipolar disorder at the human serotonin transporter gene (hSERT; 5HTT). Mol Psychiatry. 1997; 2(5): 398–402.
33. Hoene M R, Wendel B, Grunewald I, Chiaroni P, Levy N, Morris-Rosendahl D, Macher J P, Sander T, Crocq M A Serotonin transporter (5HTT) gene polymorphisms are not associated with susceptibility to mood disorders. Am J Med Genet. 1998; 81: 1–3.
34. Gutierrez B, Arranz M J, Collier D, Valles V, Guillamant R, Bertranpetit J, Murray R, Fananas L. Serotonin transporter gene and risk for bipolar affective disorder: an association study in a Spanish population. Biol Psychiatry. 1998; 43: 843–847.
35. Vincent J B, Masellis M, Lawrence J, Choi V, Gurling H MD, Phil M, Parikh S V, Kennedy J L. Genetic association analysis of serotonin system genes in bipolar affective disorders. Am J Psychiatry. 1999; 156: 136–138.
36. Furlong R A, Ho L, Walsh C, Rubinsztein J S, Jain S, Paykel E S, Easton D F, Rubinsztein D C. Analysis and meta-analysis of two serotonin transporter gene polymorphisms in bipolar and unipolar affective disorder. Am J Med Genet. 1998; 81(1): 58–63.
37. Smeraldi E, Zanardi R, Benedetti F, Di Bella D, Perez J, Catalano M. Polymorphism within the serotonin transporter and antidepressant efficacy of fluvoxamine. Mol Psychiatry. 1998; 3(6): 508–511.
38. Zanardi R, Benedetti F, Di Bella D, Catalano M, Smeraldi E. Efficacy of paroxetine in depression is influenced by a functional polymorphism within the promoter of the serotonin transporter gene. J Clin Psychopharmacol. 2000; 20(1): 105–107.
39. Benedetti F, Serretti A, Colombo C, Campori E, Barbini B, Di Bella D, Smeraldi E. Influence of a functional polymorphism within the promoter of the serotonin transporter gene on the effects of total sleep deprivation in bipolar depression. Am J Psychiatry. 1999; 156(9): 1450–1452.
40. Kelsoe J R. Promoter prognostication: the serotonin transporter gene and antidepressant response. Mol Psychiatry. 1998; 3: 475–476.
41. American Psychiatric Association. Diagnostic and Statistical Manual of Mental Disorders. Fourth Edition. Washington, D.C.: American Psychiatric Association; 1994.
42. Maxwell ME and the NIMH Molecular Genetics Initiative. Family Interview for Genetic Studies. 1992.
43. Lahiri D K, Nurnberger J I. A rapid no-enzymatic method for the preparation of HMW DNA from blood for RFLP analysis. Nucd Acids Res. 1991; 19: 5444.
44. Cook E H Jr, Courchesne R, Lord C, Cox N J, Yan S, Lincoln A, Haas R, Courchesne E, Leventhal B L. Evidence of linkage between the serotonin transporter and autistic disorder. Mol Psychiatry. 1997; 2: 247–250.
45. Beique J C, Lavoie N, de Montigny C, Debonnel G. Affinities of venlafaxine and various reuptake inhibitors for the serotonin and norepinephrine transporters. Eur J Pharmacol. 1988; 349(1): 129–132.
46. Owens M J, leni J R, Knight D L, Winders K, Nemeroff C B. The serotonergic antidepressant nefazodone inhibits the serotonin transporter: in vivo and ex vivo studies. Life Sci. 1995; 57(24): 373–380.
47. Kim D K, Lim S W, Lee S, Sohn S E, Kim S, Hahn C G, Carroll B J. Serotonin transporter gene polymorphism and antidepressant response. Neuroreport. 2000: 11(1): 215–219.
48. Coryell W, Endicott J, Keller M. Rapid cycling affective disorder: demographics, diagnosis, family history and course. Arch Gen Psychiatry. 1992; 49: 126–131.
49. Heils A, Teufel A, Petri S, Strober G, Riederer P, Bengel D, Lesch K P. Allelic variation of human serotonin transporter gene expression. J. Neurochemistry (1996) 66: 2621–2624.
50. Mundo E, Walker M, Cate T, Macciardi F, Kennedy J L (2001). The role of the serotonin transporter protein gene in antidepressant-induced mania in Bipolar Disorder: preliminary findings. *The Archives of General Psychiatry*, 58: 539–544.

We claim:
1. A method of determining the susceptibility of a patient to antidepressant-induced mania comprising:
   (a) obtaining a sample from the patient; and
   (b) testing the sample for the presence of the s variant of the 5HTTLPR polymorphism in the 5HTT gene, wherein the presence of the s variant indicates that the patient is more susceptible to antidepressant-induced mania;
   wherein the patient has a Bipolar Disorder and is treated with an antidepressant that is a pro-serotonergic agent.
2. A method according to claim 1 wherein the pro-serotonergic agent is clomipramine, fluvoxamine, fluoxet- ine, paroxetine, sertraline, citalopram, imipramine, nefazodone, vanlafaxine or moclobemide.

3. A method according to claim 1 wherein the sample is blood.

4. A method according to claim 1 wherein step (b) comprises (i) extracting nucleic acids from the sample: (ii) amplifying the extracted nucleic acids using polymerase chain reaction (PCR); (iii) performing electrophoresis of the PCR products; and (iv) determining the presence of the polymorphism.

* * * * *

SEQUENCE LISTING

```
<160> NUMBER OF SEQ ID NOS: 1

<210> SEQ ID NO 1
<211> LENGTH: 366
<212> TYPE: DNA
<213> ORGANISM: Homo sapiens
<220> FEATURE:
<221> NAME/KEY: misc_feature
<222> LOCATION: (199)..(199)
<223> OTHER INFORMATION: n is a, c, g, or t

<400> SEQUENCE: 1
ctaatgtccc tactgcagcc ctcccagcat cccccctgca acctcccagc aactccctgt      60 accctccta ggatcgctcc tgcatccccc attatccccc ccttcaccccc tcgcggcatc     120 cccctgcac ccccagcatc cccctgcag cccttccagc atcccctgc acctctccca       180 ggatattccc tgcaacacnc attattcccc ctgcaccct cgcagtattc cccctgcacc     240
ccccagcatc ccccatgca cccccggcat cccccctgca ccctccagc attctcctttg    300 caccctacca gtattccccc gcatcccggc ctccaagcct cccgcccgac ctctgtcacc    360
gccctg                                                              366
```